United States Patent
Mankovitz

(10) Patent No.: US 6,783,754 B2
(45) Date of Patent: Aug. 31, 2004

(54) PLANT-BASED NON-TOXIC SUNSCREEN PRODUCTS

(76) Inventor: Roy J. Mankovitz, 24236 Park Granada, Calabasas, CA (US) 91302

( * ) Notice: Subject to any disclaimer, the term of this patent is extended or adjusted under 35 U.S.C. 154(b) by 54 days.

(21) Appl. No.: 10/167,033

(22) Filed: Jun. 11, 2002

(65) Prior Publication Data

US 2002/0187114 A1 Dec. 12, 2002

Related U.S. Application Data

(60) Provisional application No. 60/297,377, filed on Jun. 11, 2001.

(51) Int. Cl.⁷ .............................. A61K 7/42; A61K 7/44; A61K 7/00; A61K 35/78
(52) U.S. Cl. ........................... 424/59; 424/60; 424/400; 424/401; 424/725
(58) Field of Search .......................... 424/59, 60, 400, 424/401, 725, 196.1

(56) References Cited

U.S. PATENT DOCUMENTS

| | | | |
|---|---|---|---|
| 4,258,055 A | 3/1981 | Lietti et al. | 424/283 |
| 4,376,781 A | 3/1983 | Lietti et al. | 424/283 |
| 4,413,004 A | 11/1983 | Lietti et al. | 424/283 |
| 5,780,060 A | 7/1998 | Levy et al. | 424/489 |
| 5,804,168 A | 9/1998 | Murad | 424/59 |
| 5,853,728 A | 12/1998 | Tanabe et al. | 424/195.1 |
| 6,471,949 B2 * | 10/2002 | Candau et al. | 424/59 |

* cited by examiner

*Primary Examiner*—Shelley A. Dodson
(74) *Attorney, Agent, or Firm*—Gifford, Krass, Groh, Sprinkle, Anderson & Citkowski, PC

(57) ABSTRACT

A method for protecting against UV radiation includes the steps of extracting a cyanin from a plant and applying it to the skin to act as a sunshield. In the preferred embodiments, the plant cyanin is selected from anthocyanin and betacyanin. Optionally, the plant cyanin is derived from a tropical plant, illustratively including the palm family, tropical fruit and nut bearing plants and flowering plants. A sunscreen composition is provided including a plant derived cyanin and a skin-compatible carrier. Optionally, the cyanin is selected from an anthocyanin and a betacyanin, which is present at a concentration ranging from 0.05% to 75% of the weight of the total composition. A sunscreen composition includes the skin-compatible carrier at a concentration ranging from 25% to 99.95% of the weight of the total composition. As a further option, a sunscreen composition includes an ingredient selected from a buffering agent, an emulsifier, a carrier, a fragrance component, a preservative, a solvent, an emollient, a pH adjusting agent, an antioxidant, a propellant, a surfactant, a thickener, a neutralizer and a mixture of any of these.

11 Claims, No Drawings

PLANT-BASED NON-TOXIC SUNSCREEN PRODUCTS

REFERENCE TO RELATED APPLICATION

This application claims priority from U.S. Provisional Patent Application Serial No. 60/297,377, filed Jun. 11, 2001. The entire content of this application is incorporated herein by reference.

FIELD OF THE INVENTION

The present invention relates to sunscreen compositions including a tropical plant cyanin. The invention further relates to methods of limiting skin exposure to ultraviolet light by topical application of a tropical plant cyanin.

BACKGROUND OF THE INVENTION

Skin cancer is on the rise, and everyone is being told to use sunblock/sunscreen daily. However, there is inconclusive evidence that sunscreen use actually results in reduced incidence of cancer. Further, there is evidence that the most popular ingredients in sunscreens, titanium dioxide, and octyl methoxycinnamate themselves become toxic and possibly carcinogenic when exposed to UV radiation.

SUMMARY OF THE INVENTION

A method is provided for protecting against UV radiation that includes the steps of extracting a cyanin from a plant and applying it to the skin to act as a sunshield. A plant cyanin is selected from anthocyanin and betacyanin. Optionally, the plant cyanin is derived from a tropical plant, illustratively including the palm family, tropical fruit and nut bearing plants and flowering plants.

A sunscreen composition is provided including a plant derived cyanin and a skin-compatible carrier. Optionally, the cyanin is selected from an anthocyanin and a betacyanin, which is present at a concentration ranging from 0.05% to 75% of the weight of the total composition. A sunscreen composition includes the skin-compatible carrier at a concentration ranging from 25% to 99.95% of the weight of the total composition. As a further option, a sunscreen composition includes an ingredient selected from a buffering agent, an emulsifier, a carrier, a fragrance component, a preservative, a solvent, an emollient, a pH adjusting agent, an antioxidant, a propellant, a surfactant, a thickener, a neutralizer and a mixture of any of these.

DESCRIPTION OF THE INVENTION

Plants, and particularly tropical plants, possess a strong ability to withstand large amounts of UV radiation without damage. Some research points to cyanins such as anthocyanin and betacyanin as perhaps the active portions of the plant responsible for at least some of the UV protection. In the present invention, tropical plant leaves, blossoms, fruit, seeds and bark are employed singly and in combination to form a non-toxic topical preparation for application to human skin to protect it from sunburn and DNA damage caused by excessive exposure to UV radiation.

The continual exposure of tropical plants to UV rays necessitates better plant adaptions for protecting exposed portions of the plants. The development of cyanins with superior UV absorbing properties may be one such adaptation and this is one reason that a tropical plant cyanin is preferred in a sunscreen composition and used in a method of the present invention over cyanins derived from non-tropical plants. A cyanin operative in a composition and method of the present invention illustratively includes an anthocyanin and a betacyanin purified from a tropical plant.

In particular, the tropical plant portions mentioned above are subjected to one or more processes to extract fluid suitable for use as a topical preparation, such as the application of pressure by an expellor press to squeeze fluid from the plant, the application of heat to extract the fluids, and the application of non-toxic chemical solvents to dissolve the desired fluid. Exemplary methods for extracting and purifying plant anthocyanins and/or betacyanins include those detailed in U.S. Pat. Nos. 4,409,254; 5,089,410; 4,211,577; 4,302,200.

A cyanin is included in a composition of the present invention at concentrations ranging from 0.05% to 75% by weight of the total composition. Preferably, a cyanin is included at concentrations ranging from 0.25% to 25%. More preferably, a cyanin is included at concentrations ranging from 0.5% to 10%.

Examples of candidate tropical plants include the trees from the palm family, tropical fruit and nut bearing plants (such as papaya, guava, pomegranate, kukui, star fruit, macadamia, banana, pineapple, and kiwi), and flowering plants (such as hibiscus, orchid, poinciana, and jacaranda). Further examples of tropical plants containing cyanins are found in the following references: Judd, W. S. et al., 1999. Plant Systematics: A Phylogenetic Approach. Sinauer Publishing; Keller, Roland, 1996. Identification of tropical woody plants in the absence of flowers and fruits. Birkhauser Verlag: Basel; Mabberley, D. J., 1997, The Plant Book; a portable dictionary of the vascular plants $2^{nd}$ Edition. Cambridge University Press; Heywood, V. H., 1993, Flowering Plants of the World. Oxford University Press; Ulrich Luttge, Physiological Ecology of Tropical Plants Springer Verlag; (1997); Micahel J. Balick, Hans T. Beck (Editors) Useful Palms of the World (Biology and Resource Management Series) Columbia University Press; (1990)

The resultant plant extract, when applied as a topical preparation, acts to protect the skin from UV damage in much the same way that tropical plants are protected, while maintaining a non-toxic environment. A composition of the present invention also optionally include other skin-compatible ingredients such as those found in The CTFA International Cosmetic Ingredient Dictionary and Handbook, 9th Edition, 2002. Such ingredients illustratively include: a buffering agent, an emulsifier, a carrier, a fragrance component, a preservative, a solvent, an emollient, a pH adjusting agent, an antioxidant, a propellant, a surfactant, a thickener or gelling agent and a neutralizer, and mixtures of any of these as appropriate for a particular application.

One type of carrier, an emollient, is oily substance which aids in application of a composition and which acts to smooth and soften the skin. Emollients are well known in the preparation of topical formulations and a suitable choice for inclusion in a composition of the present invention will be recognized as such by one of skill in the art. Illustrative examples include hydrocarbons such as C8–C30 saturated or unsaturated fatty acids or esters, such as isopropyl myristate; and mixtures thereof including those found in oils such as vegetable oils, and mineral oil. Vegetable oils illustratively include corn, safflower, coconut, soybean, cottonseed, peanut, almond, olive and the like. A skin-compatible carrier may be present at a concentration ranging from 25% to 99.95% of the weight of the total composition, depending on the concentrations of other composition components.

A composition according to the present invention includes a thickener or gelling agent such as Carbopol 980NF or an art recognized equivalent. A neutralizer may be added following dispersion of the thickener. For example, triethanolamine or an art recognized equivalent is useful in neutralizing an inventive composition.

A composition according to the present invention may be prepared by inclusion of liposomes or liposomal gel preparation. Examples of known methods of liposome preparation are described in Liposomes: A Practial Approach, R.R.C. New, Editor, Oxford University Press, 1990, 1997. The extracts may be mixed with a wide range of topical vehicles to enhance the ease of application, and may also be combined with a variety of cosmetic preparations such as moisturizers, and makeup. Coloring agents may also be added to tint the final product.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. A method of protecting against UV radiation, comprising the steps of:
   extracting a cyanin from a plant; and
   applying it to the skin to act as a sunshield.

2. The method of claim 1, wherein the cyanin is selected from the group consisting of: anthocyanin, betacyanin and a mixture thereof.

3. The method of claim 1, wherein the step of extracting a cyanin from a plant includes one or more of the following:
   squeezing a cyanin-containing fluid from the plant,
   applying heat to extract the fluid, or applying a non-toxic chemical solvent to dissolve the desired fluid.

4. The method of claim 1, wherein the plant is a tropical plant.

5. The method of claim 4, wherein the plant is chosen from the following:
   trees from the palm family,
   tropical fruit and nut bearing plants (such as papaya, guava, pomegranate, kukui, star fruit, macadamia, banana, pineapple, and kiwi), and
   flowering plants (such as hibiscus, orchid, poinciana, and jacaranda).

6. A sunscreen composition comprising:
   a cyanin derived from a plant; and
   a skin-compatible carrier.

7. The sunscreen composition of claim 6 wherein the cyanin is selected from the group consisting of: an anthocyanin and a betacyanin.

8. The sunscreen composition of claim 6 wherein the cyanin is present at a concentration ranging from 0.05% to 75% of the weight of the total composition.

9. The sunscreen composition of claim 6 wherein the skin-compatible carrier is present at a concentration ranging from 25% to 99.95% of the weight of the total composition.

10. The sunscreen composition of claim 6 further comprising an ingredient selected from the group consisting of: a buffering agent, an emulsifier, a carrier, a fragrance component, a preservative, a solvent, an emollient, a pH adjusting agent, an antioxidant, a propellant, a surfactant, a thickener, a neutralizer and a mixture thereof.

11. The sunscreen composition of claim 6 wherein the plant is a tropical plant.

* * * * *